(12) United States Patent
Schuessler et al.

(10) Patent No.: US 11,160,630 B2
(45) Date of Patent: Nov. 2, 2021

(54) TISSUE EXPANSION DEVICE

(71) Applicant: Allergan, Inc., Irvine, CA (US)

(72) Inventors: David J. Schuessler, Santa Ana, CA (US); Alberto J. Flores, Heredia (CR); Daniela Rodriguez, Mercedes (CR); Luis M. Solano, San Jose (CR)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 16/571,036

(22) Filed: Sep. 13, 2019

(65) Prior Publication Data

US 2020/0085526 A1 Mar. 19, 2020

Related U.S. Application Data

(60) Provisional application No. 62/731,033, filed on Sep. 13, 2018.

(51) Int. Cl.
*A61B 90/00* (2016.01)
*A61F 2/10* (2006.01)
*A61F 2/12* (2006.01)

(52) U.S. Cl.
CPC ............ *A61B 90/02* (2016.02); *A61F 2/105* (2013.01); *A61F 2/12* (2013.01);
(Continued)

(58) Field of Classification Search
CPC ...... A61B 90/02; A61F 2/12; A61F 2250/006; A61F 2250/0058; A61F 2250/0097; A61F 2250/0025
See application file for complete search history.

(56) References Cited

U.S. PATENT DOCUMENTS 3,204,959 A 9/1965 Nichols
3,301,251 A 1/1967 Jackson
(Continued)

FOREIGN PATENT DOCUMENTS

EP 0029292 5/1981
EP 0324234 7/1989
(Continued)

OTHER PUBLICATIONS

"Tacky Gels for Healthcare Applications," Silicone-Polymers, NuSil Silicone Technology, 2009, www.silicone-polymers.com/pdf2009/Tacky%20Gels%20for%20Healthcare%20Applications.pdf, 3 pages.
(Continued)

*Primary Examiner* — Jerrah Edwards
*Assistant Examiner* — Jared Klar Rovira
(74) *Attorney, Agent, or Firm* — Nathan S. Smith; Danny Mansour; Morgan, Lewis & Bockius LLP

(57) ABSTRACT

A tissue expansion device can be implanted temporarily beneath skin of a patient and removed upon predetermined expansion of overlying tissue. The device can include an expandable shell having a smooth or glossy outer surface and an injection port. The expandable shell can form an expandable chamber and have an anterior portion and a posterior portion. The injection port can be coupled to the anterior portion of the shell and be in fluid communication with the chamber and configured to permit injection of fluid into the chamber from a hypodermic needle. The device can have a plurality of tabs coupled to the posterior portion of the shell having one or more colors or attributes. The device can also include an orientation indicator visible along the anterior portion of the shell for assisting a clinician and orienting the device during the implantation procedure.

24 Claims, 10 Drawing Sheets

(52) U.S. Cl.
CPC ........... *A61F 2250/0006* (2013.01); *A61F 2250/0025* (2013.01); *A61F 2250/0058* (2013.01); *A61F 2250/0097* (2013.01)

(56) References Cited

U.S. PATENT DOCUMENTS

| | | | |
|---|---|---|---|
| 3,301,254 A | 1/1967 | Schickedanz | |
| 3,577,836 A | 5/1971 | Tamura | |
| 3,852,832 A | 12/1974 | McGhan et al. | |
| 3,919,724 A | 11/1975 | Sanders et al. | |
| 4,125,117 A * | 11/1978 | Lee | A61F 2/52 |
| | | | 450/54 |
| 4,157,085 A | 6/1979 | Austad | |
| 4,190,040 A | 2/1980 | Schulte | |
| 4,195,639 A | 4/1980 | Lee | |
| 4,200,098 A | 4/1980 | Ayer et al. | |
| 4,332,634 A | 6/1982 | Aperavich | |
| 4,428,364 A | 1/1984 | Bartolo | |
| 4,455,691 A | 6/1984 | Van Aken Redinger et al. | |
| 4,605,412 A | 8/1986 | LaForest et al. | |
| 4,636,213 A | 1/1987 | Pakiam | |
| 4,650,487 A | 3/1987 | Chaglassian | |
| 4,662,357 A | 5/1987 | Pierce et al. | |
| 4,685,447 A | 8/1987 | Iversen et al. | |
| 4,738,657 A | 4/1988 | Hancock et al. | |
| 4,773,909 A | 9/1988 | Chaglassian | |
| 4,823,815 A | 4/1989 | Watson et al. | |
| 4,840,615 A | 6/1989 | Hancock et al. | |
| 4,889,744 A | 12/1989 | Quaid | |
| 4,908,029 A | 3/1990 | Bark et al. | |
| 4,960,425 A | 10/1990 | Yan et al. | |
| 4,969,906 A | 11/1990 | Kronman | |
| 5,005,591 A | 4/1991 | Austad | |
| 5,019,101 A | 5/1991 | Purkait et al. | |
| 5,022,942 A | 6/1991 | Yan et al. | |
| 5,026,394 A | 6/1991 | Baker | |
| 5,066,303 A | 11/1991 | Bark et al. | |
| 5,074,878 A | 12/1991 | Bark et al. | |
| 5,084,061 A | 1/1992 | Gau et al. | |
| 5,127,627 A | 7/1992 | Wiser | |
| 5,133,753 A | 7/1992 | Bark et al. | |
| 5,141,508 A | 8/1992 | Bark et al. | |
| 5,171,269 A | 12/1992 | Bark | |
| 5,282,857 A | 2/1994 | Perry et al. | |
| 5,340,352 A | 8/1994 | Nakanishi et al. | |
| 5,425,762 A | 6/1995 | Muller | |
| 5,447,535 A | 9/1995 | Muller | |
| 5,456,716 A | 10/1995 | Iversen et al. | |
| 5,480,430 A | 1/1996 | Carlisle et al. | |
| 5,496,368 A | 3/1996 | Wiese | |
| 5,525,275 A | 6/1996 | Iversen et al. | |
| 5,536,264 A | 7/1996 | Hsueh et al. | |
| 5,549,672 A | 8/1996 | Maddock et al. | |
| 5,571,183 A | 11/1996 | Kazem | |
| 5,589,176 A | 12/1996 | Seare, Jr. | |
| 5,632,774 A | 5/1997 | Babian | |
| 5,658,329 A | 8/1997 | Purkait | |
| 5,674,279 A | 10/1997 | Wright et al. | |
| 5,674,285 A | 10/1997 | Quaid | |
| 5,725,507 A | 3/1998 | Petrick | |
| 5,895,423 A | 4/1999 | Becker et al. | |
| 5,964,803 A | 10/1999 | Iversen et al. | |
| 6,022,376 A | 2/2000 | Assell et al. | |
| 6,074,421 A | 6/2000 | Murphy | |
| 6,146,418 A | 11/2000 | Berman | |
| 6,203,570 B1 | 3/2001 | Baeke | |
| 6,214,045 B1 | 4/2001 | Corbitt, Jr. et al. | |
| 6,214,331 B1 | 4/2001 | Vanderhoff et al. | |
| 6,228,116 B1 | 5/2001 | Ledergerber | |
| 6,231,712 B1 | 5/2001 | Torres | |
| 6,232,372 B1 | 5/2001 | Brothers et al. | |
| 6,287,293 B1 | 9/2001 | Jones et al. | |
| 6,371,904 B1 | 4/2002 | Sirimanne et al. | |
| 6,588,432 B1 | 7/2003 | Rehder et al. | |
| 6,602,452 B2 | 8/2003 | Schuessler | |
| 6,605,116 B2 | 8/2003 | Falcon et al. | |
| 6,692,527 B1 | 2/2004 | Bellin et al. | |
| 6,692,528 B2 | 2/2004 | Ward et al. | |
| 6,733,512 B2 | 5/2004 | McGhan | |
| 6,743,254 B2 | 6/2004 | Guest et al. | |
| 6,755,861 B2 | 6/2004 | Nakao | |
| 6,913,765 B2 | 7/2005 | Li et al. | |
| 6,955,690 B1 | 10/2005 | Cao | |
| 6,962,739 B1 | 11/2005 | Kim et al. | |
| 7,018,692 B2 | 3/2006 | Kim et al. | |
| 7,058,439 B2 | 6/2006 | Eaton et al. | |
| 7,081,135 B2 * | 7/2006 | Smith | A61F 2/12 |
| | | | 606/151 |
| 7,238,193 B2 | 7/2007 | Gedebou | |
| 7,645,475 B2 | 1/2010 | Prewett | |
| 7,702,378 B2 | 4/2010 | Bolan et al. | |
| 7,771,462 B1 | 8/2010 | Davidson et al. | |
| 7,785,302 B2 | 8/2010 | Sheetz et al. | |
| 7,810,223 B2 | 10/2010 | Hemerick | |
| 7,914,578 B2 | 3/2011 | Vardi | |
| 7,976,859 B2 | 7/2011 | Beisang et al. | |
| 8,021,418 B2 | 9/2011 | Gerberding et al. | |
| 8,027,712 B2 | 9/2011 | Sioshansi et al. | |
| 8,066,758 B2 | 11/2011 | Bogert et al. | |
| 8,070,809 B2 | 12/2011 | Schuessler | |
| 8,202,259 B2 | 6/2012 | Sheetz et al. | |
| 8,320,993 B2 | 11/2012 | Sirimanne et al. | |
| 8,343,205 B2 | 1/2013 | Sugimoto et al. | |
| 8,377,127 B2 | 2/2013 | Schuessler | |
| 8,382,723 B2 | 2/2013 | Powers et al. | |
| 8,398,710 B2 | 3/2013 | Forsell | |
| 8,454,690 B2 | 6/2013 | McClellan | |
| 8,463,357 B2 | 6/2013 | Piran et al. | |
| 8,506,627 B2 * | 8/2013 | Van Epps | A61F 2/12 |
| | | | 623/8 |
| 8,609,004 B2 | 12/2013 | Schuessler | |
| 8,636,797 B2 | 1/2014 | Chitre et al. | |
| 8,670,633 B2 | 3/2014 | Boyden et al. | |
| 8,690,943 B2 | 4/2014 | Schuessler | |
| 8,784,486 B2 | 7/2014 | Schuessler | |
| 8,821,574 B2 | 9/2014 | Davodian | |
| 8,852,276 B2 | 10/2014 | Del Vecchio | |
| 8,875,714 B2 | 11/2014 | Boyden et al. | |
| 8,920,486 B2 | 12/2014 | Park | |
| 8,968,400 B2 | 3/2015 | Schuessler | |
| 9,138,311 B2 | 9/2015 | Van Epps et al. | |
| 9,241,773 B2 | 1/2016 | Bolan et al. | |
| 9,380,998 B2 | 7/2016 | Sirimanne et al. | |
| 9,387,068 B2 | 7/2016 | Schuessler | |
| 9,393,106 B2 | 7/2016 | Van Epps et al. | |
| 9,399,122 B2 | 7/2016 | Mosharrafa et al. | |
| 9,463,087 B2 | 10/2016 | Hristov et al. | |
| 9,480,584 B2 | 11/2016 | Park | |
| 9,532,888 B2 | 1/2017 | Dugan et al. | |
| 9,603,698 B2 | 3/2017 | Kerr et al. | |
| 9,630,366 B2 | 4/2017 | Schuessler | |
| 9,636,210 B2 | 5/2017 | Hristov et al. | |
| 9,669,117 B2 | 6/2017 | Campbell et al. | |
| 9,682,186 B2 | 6/2017 | Powers et al. | |
| 9,700,404 B2 | 7/2017 | Martin et al. | |
| 9,700,405 B2 | 7/2017 | Davila et al. | |
| 9,713,524 B2 | 7/2017 | Glicksman | |
| 9,724,189 B2 | 8/2017 | Forsell | |
| 9,750,600 B2 * | 9/2017 | Mayo Martin | A61F 2/12 |
| 9,775,704 B2 | 10/2017 | Bergheim et al. | |
| 9,814,566 B1 | 11/2017 | Cree | |
| 9,848,972 B2 | 12/2017 | Van Epps | |
| 9,884,150 B2 | 2/2018 | Jho et al. | |
| 9,918,829 B2 | 3/2018 | Van Epps et al. | |
| 10,182,904 B2 | 1/2019 | Gliner et al. | |
| 2001/0052141 A1 | 12/2001 | Andersen | |
| 2002/0106953 A1 | 8/2002 | Kim et al. | |
| 2003/0093151 A1 | 5/2003 | Zhang | |
| 2003/0134067 A1 | 7/2003 | Garelli | |
| 2003/0144734 A1 | 7/2003 | Dreschnack et al. | |
| 2003/0149481 A1 | 8/2003 | Guest et al. | |
| 2003/0171768 A1 | 9/2003 | McGhan | |
| 2003/0205846 A1 | 11/2003 | Bellin et al. | |
| 2003/0233150 A1 | 12/2003 | Bourne et al. | |

(56) References Cited

U.S. PATENT DOCUMENTS

| | | |
|---|---|---|
| 2005/0170221 A1 | 8/2005 | Kim et al. |
| 2007/0059375 A1 | 3/2007 | Bourne et al. |
| 2007/0156230 A1 | 7/2007 | Dugan et al. |
| 2007/0196454 A1 | 8/2007 | Stockman et al. |
| 2007/0198085 A1 | 8/2007 | Benslimane |
| 2007/0233273 A1* | 10/2007 | Connell ............... A61F 2/12 623/23.72 |
| 2008/0027534 A1 | 1/2008 | Edwin et al. |
| 2008/0063716 A1 | 3/2008 | Moro et al. |
| 2008/0312739 A1 | 12/2008 | Agerup et al. |
| 2009/0012372 A1 | 1/2009 | Burnett et al. |
| 2009/0030515 A1 | 1/2009 | Schuessler et al. |
| 2009/0048684 A1 | 2/2009 | Lesh |
| 2009/0118756 A1 | 5/2009 | Valencon et al. |
| 2009/0118829 A1 | 5/2009 | Powell et al. |
| 2009/0198332 A1 | 8/2009 | Becker |
| 2009/0198333 A1 | 8/2009 | Becker |
| 2009/0202608 A1 | 8/2009 | Alessi et al. |
| 2009/0270904 A1 | 10/2009 | Birk et al. |
| 2009/0270985 A1 | 10/2009 | Schuessler |
| 2009/0275974 A1 | 11/2009 | Marchand et al. |
| 2009/0326654 A1 | 12/2009 | Powell |
| 2010/0049316 A1 | 2/2010 | Schuessler |
| 2010/0070042 A1 | 3/2010 | Bryan et al. |
| 2010/0168853 A1 | 7/2010 | Job |
| 2011/0054407 A1 | 3/2011 | Olroyd |
| 2011/0153017 A1* | 6/2011 | McClellan ............ A61B 90/02 623/8 |
| 2011/0270391 A1 | 11/2011 | Chitre et al. |
| 2011/0288639 A1 | 11/2011 | Trilokekar et al. |
| 2011/0306827 A1 | 12/2011 | Chitre et al. |
| 2012/0061368 A1 | 3/2012 | Frigerio et al. |
| 2012/0109080 A1 | 5/2012 | Manesis et al. |
| 2012/0123537 A1 | 5/2012 | Manesis et al. |
| 2012/0197393 A1 | 8/2012 | Yu |
| 2012/0277858 A1* | 11/2012 | Brinon ................. A61F 2/12 623/8 |
| 2012/0303120 A1 | 11/2012 | Schuessler |
| 2013/0052142 A1 | 2/2013 | Harder et al. |
| 2013/0131799 A1 | 5/2013 | Schuessler |
| 2013/0131801 A1 | 5/2013 | Schuessler |
| 2013/0171288 A1 | 7/2013 | Harders |
| 2013/0245758 A1 | 9/2013 | Chitre et al. |
| 2013/0304207 A1 | 11/2013 | Schuessler |
| 2013/0325120 A1 | 12/2013 | McClellan |
| 2014/0257481 A1 | 9/2014 | Brooks et al. |
| 2016/0000547 A1 | 1/2016 | Aiden et al. |
| 2016/0074152 A1 | 3/2016 | Chitre et al. |
| 2016/0262835 A1 | 9/2016 | Davila et al. |
| 2017/0014226 A1 | 1/2017 | Fenaroli |
| 2017/0035999 A1 | 2/2017 | Wijay |
| 2017/0042707 A1 | 2/2017 | Park |
| 2017/0189165 A1 | 7/2017 | Hristov et al. |
| 2017/0265990 A1 | 9/2017 | Martin et al. |
| 2017/0319328 A1 | 11/2017 | Davila et al. |
| 2017/0348089 A1 | 12/2017 | Becker |
| 2018/0036122 A1 | 2/2018 | Bergheim et al. |
| 2018/0256276 A1 | 9/2018 | Zamarripa et al. |
| 2019/0142574 A1* | 5/2019 | Quiros ............... A61L 27/18 623/8 |

FOREIGN PATENT DOCUMENTS

| | | |
|---|---|---|
| EP | 0412703 | 2/1991 |
| EP | 0422302 | 4/1991 |
| EP | 0478279 | 4/1992 |
| EP | 0710468 | 5/1996 |
| EP | 0784987 | 7/1997 |
| EP | 0872221 | 2/1999 |
| EP | 1469799 B1 | 5/2014 |
| EP | 2531254 B1 | 5/2015 |
| EP | 2928412 B1 | 3/2017 |
| EP | 3348234 | 7/2018 |
| EP | 3125824 B1 | 10/2018 |
| EP | 2996631 B1 | 12/2019 |
| FR | 587637 | 4/1925 |
| FR | 895747 | 2/1945 |
| GB | 2040688 | 9/1980 |
| GB | 2392077 | 2/2004 |
| WO | WO 92/20519 | 11/1992 |
| WO | WO 95/01864 | 1/1995 |
| WO | WO 02/10667 | 2/2002 |
| WO | WO 2003/017868 | 3/2003 |
| WO | WO 2003/057462 | 7/2003 |
| WO | WO 2003/059617 | 7/2003 |
| WO | WO 2004/021935 | 3/2004 |
| WO | WO 2005/000165 | 1/2005 |
| WO | WO 2008/016983 | 2/2008 |
| WO | WO 2009/061672 | 5/2009 |
| WO | WO 2011/084465 | 7/2011 |
| WO | WO 2012/064683 | 5/2012 |
| WO | WO 2013/045000 | 4/2013 |
| WO | WO 2013/105083 | 7/2013 |
| WO | WO 2014/118773 | 7/2014 |
| WO | WO 2015/153066 | 10/2015 |
| WO | WO 2015/179061 | 11/2015 |
| WO | WO 2016/144475 | 9/2016 |
| WO | WO-2017196973 A2 * | 11/2017 ............... A61F 2/12 |
| WO | WO 2017/214113 | 12/2017 |
| WO | WO 2018/097891 | 5/2018 |

OTHER PUBLICATIONS

Sientra Inc., "Breast Implants and Tissue Expanders Product Catalog," Jan. 2012, retrieved from https://vdocuments.mx/download/breast-implants-and-tissue-expanders-product-expanders-silicone-breast-implants, pp. 20-28.

* cited by examiner

TISSUE EXPANSION DEVICE

CROSS-REFERENCE TO RELATED APPLICATIONS

This application claims the benefit of and priority to related U.S. Patent Provisional Application No. 62/731,033, filed on Sep. 13, 2018, the entirety of which is incorporated herein by reference.

BACKGROUND

Field

The present disclosure relates generally to systems and methods for tissue expansion, and more particularly, to expanding the tissue of a patient in preparation for receiving an implant.

Background

Implantable prostheses are commonly used to replace or augment body tissue. In the case of breast cancer, a mastectomy is sometimes necessary to remove some or all of the mammary gland and surrounding tissue, which creates a void. This void may be filled with a fluid-filled implantable prosthesis. The implant serves to support surrounding tissue and to maintain the appearance of the body. The restoration of the normal appearance of the body has an extremely beneficial psychological effect on post-operative patients, alleviating much of the shock and depression that often follows extensive surgical procedures.

Soft implantable prostheses typically include a relatively thin and quite flexible envelope or shell made of silicone elastomer. The shell is filled either with a silicone gel or with a physiologic saline solution. The filling of the shell may take place before or after the shell is implanted in the patient.

A saline-filled implant includes an outer shell of several layers of silicone elastomer having a valve or fill port on one side. The prosthesis is typically implanted into the breast cavity in an empty or only partially filled state. The implant is then inflated to its final size by means of the valve or fill port. This helps reduce the size of the needed incision, and enables a surgeon to adjust and even microadjust the volume of the implant.

In breast reconstruction, prior to implantation of a long-term prosthesis, it is common practice to utilize a more temporary implant, for example, what is known as a "tissue expander" or "tissue expansion device" in order to gradually create the space necessary for the long-term prosthesis. For example, in some situations, such as a mastectomy, the chest tissues may be flat and tight, and an expander can serve to prepare the body for receiving a long-term prosthesis. Tissue expanders can also be used in other places in the body to expand healthy tissue to replace a nearby defect such as a burn or scar. Essentially, a tissue expansion device comprises an inflatable body, having an inflation valve connected thereto. The valve may be formed into the inflatable body itself or may be remotely located and connected to the inflatable body by means of an elongated conduit.

The inflatable body of the tissue expansion device is placed subcutaneously in the patient, at the location of where tissue is to be expanded. The inflation valve, whether on the implant or remote thereto, is also subcutaneously positioned or implanted, and is configured to allow gradual introduction of fluid, typically saline, into the inflation body, by injection with a syringe. After gradual inflation at pre-determined intervals, the skin and subcutaneous tissues overlying the expander are consequently caused to expand in response to the pressure exerted upon such tissues by the inflatable body as solution is gradually introduced therein.

After gradual inflation at pre-determined intervals, which may extend over weeks or months, the skin and subcutaneous tissue will expand to the point where further medical procedures can be performed, such as the implantation of a long-term prosthesis, plastic and reconstructive surgery, or for use of the skin and subcutaneous tissue for use in some other part of the body.

SUMMARY

The present application discloses various improvements for tissue expansion devices and related procedures that can be used to treat humans and/or animals. The devices and procedures can be used, for example, in the context of breast reconstruction surgery, breast augmentation surgery, and skin graft surgery.

Implantable devices, such as breast implants and tissue expansion devices, can be round or anatomically shaped. In accordance with an aspect of at least some of the embodiments disclosed herein is the realization that if anatomically shaped, breast implants are generally symmetrical about a centerline and therefore, require the surgeon to be aware of that centerline so the device is implanted in the proper orientation.

In accordance with some embodiments disclosed herein, a tissue expansion device can be configured in a manner that improves on the current state of the art by providing more effective and more economical orientation means. For example, instead of applying a separate material, such as a strip of contrasting colored material to the shell in a manufacturing step separate from the creation of the shell of the implant, the present disclosure provides devices and methods that can provide a visually contrasting line on the shell during the casting/molding process of the silicone shell.

For example, in some embodiments, a shell casting tool can be provided to create a tissue expansion device, whether it is a mold or a mandrel, which can be finished with a surface that is roughened, by sandblasting or other means, except for the desired orientation line feature which is left as a polished or glossy surface. The resulting silicone shell made from this tool can then inherently and clearly illustrate these two different surface finishes by providing a contrasting visible orientation line on the shell surface without additional components or assembly steps.

Optionally, in at least one embodiment, a tissue expansion device can be provided that comprises suture tabs placed around the periphery to help stabilize the device position upon implantation. Suture tabs can be positioned, for example, at the 6 or 12 o'clock position to provide a means of visual orientation for the clinician.

However, in accordance with at least some embodiments disclosed herein is the realization that if all the suture tabs appear the same, as in traditional devices, it is possible to inadvertently slightly rotate the device during the implantation process and mistake one suture tab for another. For example, it is possible to mistake the 6 o'clock suture tab with an adjacent suture tab, such as a 4 or 8 o'clock suture. Thus, according to some embodiments, a tissue expansion device can be provided that uses a visually distinctive, unique-looking, or differently colored suture tab at only a single position, such as at the 6 o'clock position. In this manner, a clinician can more clearly distinguish the suture tabs from each other and discern the proper orientation of the device during the procedure.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the present disclosure are described below with reference to the drawings. The illustrated embodiments are intended to illustrate, but not to limit, the present disclosure. The drawings contain the following figures.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of breast reconstruction or augmentation, such embodiments can be used with various devices and implants. Furthermore, various applications of such embodiments and modifications thereto, which may occur to those who are skilled in the art, are also encompassed by the general concepts described herein.

Figure 1:
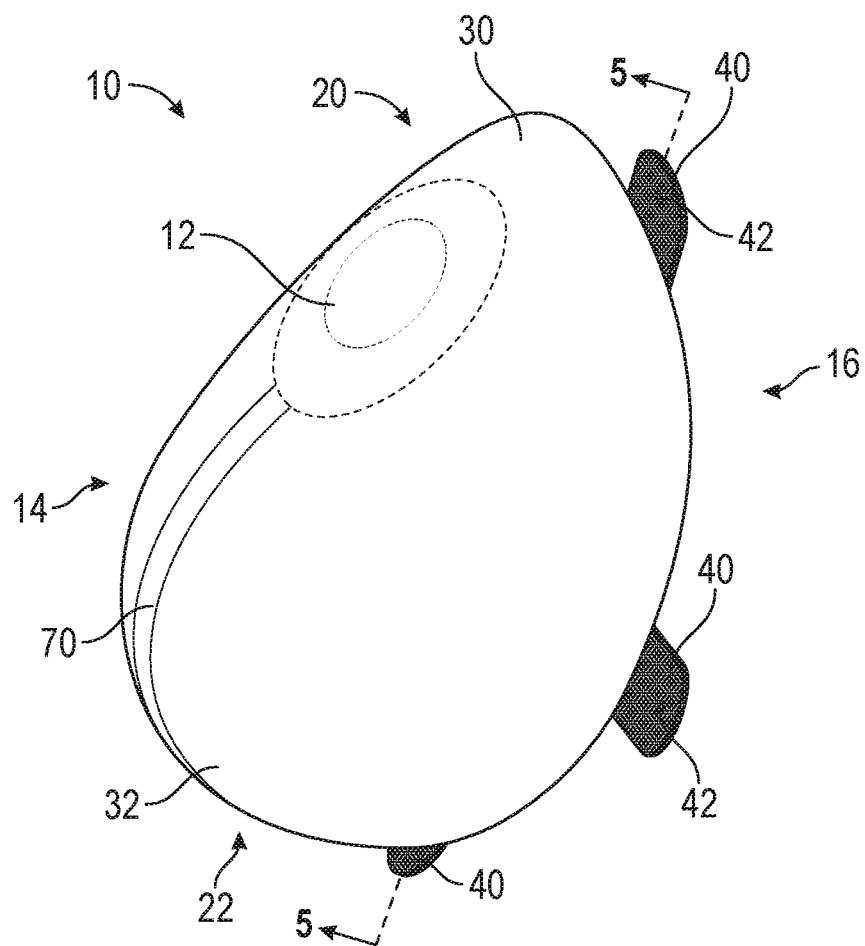
FIG. 1 is a perspective view of a tissue expansion device, according to some embodiments.

With reference now to the figures, FIG. 1 illustrates a perspective view of a tissue expansion device 10 that can be used for temporary surgical implantation in a patient, preliminary to another procedure, such as breast augmentation, breast reconstruction, or skin grafting. The tissue expansion device 10 can be placed beneath the skin and left in place for a period of time to permit overlying tissue and skin to grow or adjust to a given volume of the tissue expansion device 10.

Figure 2:
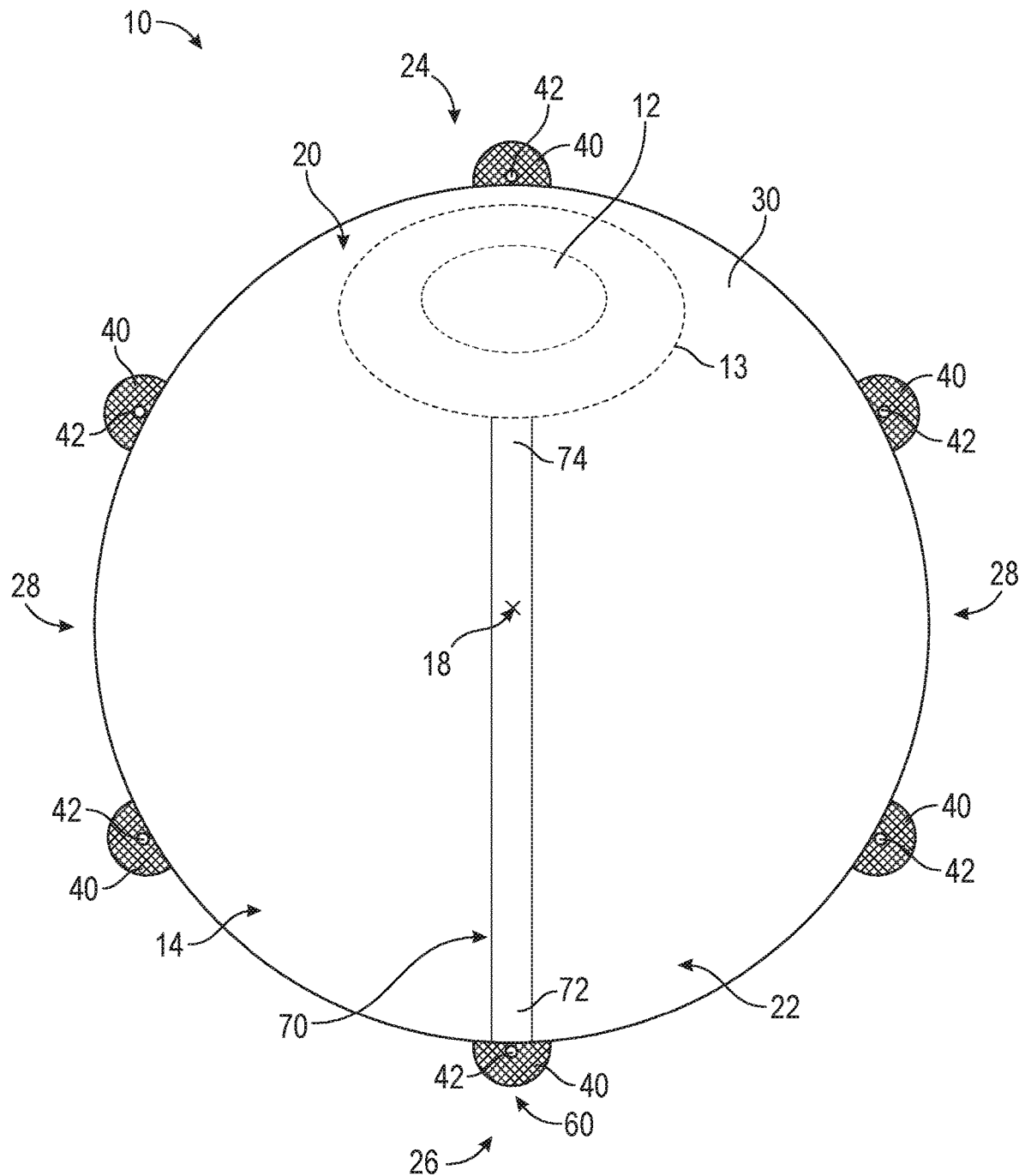
FIG. 2 is a front view of the tissue expansion device of FIG. 1, according to some embodiments.

As shown in FIGS. 1 and 2, as necessary, a clinician can inject or fill the tissue expansion device 10 with a fluid via an injection port 12 of the device 10. For example, a clinician can use a needle of a syringe to pierce the tissue expansion device 10 within the injection port 12 in order to fill the device 10. The injection port 12 can provide controllable flow into or out of the tissue expansion device 10. Further, the injection port 12 can be self-sealing upon removal of the needle.

As illustrated in FIG. 1, the tissue expansion device 10 can comprise an anterior portion 14, a posterior portion 16, an upper pole 20, and a lower pole 22. Further, the tissue expansion device 10 can also comprise an expandable shell 30. The expandable shell 30, or portions thereof, can be formed from a biocompatible polymer material such as silicone rubber, a laminate of various forms of silicone, silicone copolymers, polyurethane, and various other elastomers in various combinations.

As shown in the front view of FIG. 2, the expandable shell 30 of the tissue expansion device 10 can define a midpoint or center position 18 that lies at a position between the upper pole 20 and the lower pole 22. In some embodiments, the center position 18 of the expandable shell 30 can be located at a geometric center of a circular shell. For example, FIG. 2 illustrates that the center position 18 is located at a midpoint of the diameter between opposing edges, circumference, or boundaries of the expandable shell 30. However, in embodiments where the shell 30 is not circular, the center position 18 need not represent a geometric center of the shell; for example, the center position 18 can represent a midpoint along a line (e.g., a height dimension or diameter) extending from an edge of a top portion 24 of the shell 30 to an edge of a bottom portion 26 of the shell 30.

In accordance with at least one embodiment, an outer surface 32 of the shell 30 can have a smooth or glossy finish. The device 10 can be round, circular, oval, crescent-shaped, anatomically shaped, or other suitable shapes in order to mimic a natural or desired breast shape.

In at least one embodiment, the tissue expansion device 10 can comprise a plurality of tabs 40 coupled to the posterior portion 16 of the shell 30. The tabs 40 can be used by the clinician to anchor, engage, or secure the tissue expansion device 10 relative to the surrounding tissue at the implantation site of the patient. As shown in FIGS. 1 and 2, the tabs 40 can optionally comprise an aperture 42 through which a suture or other fastening means can be coupled to the tab 40 to facilitate anchoring of the tissue expansion device 10 to the patient's tissue.

Figure 3:
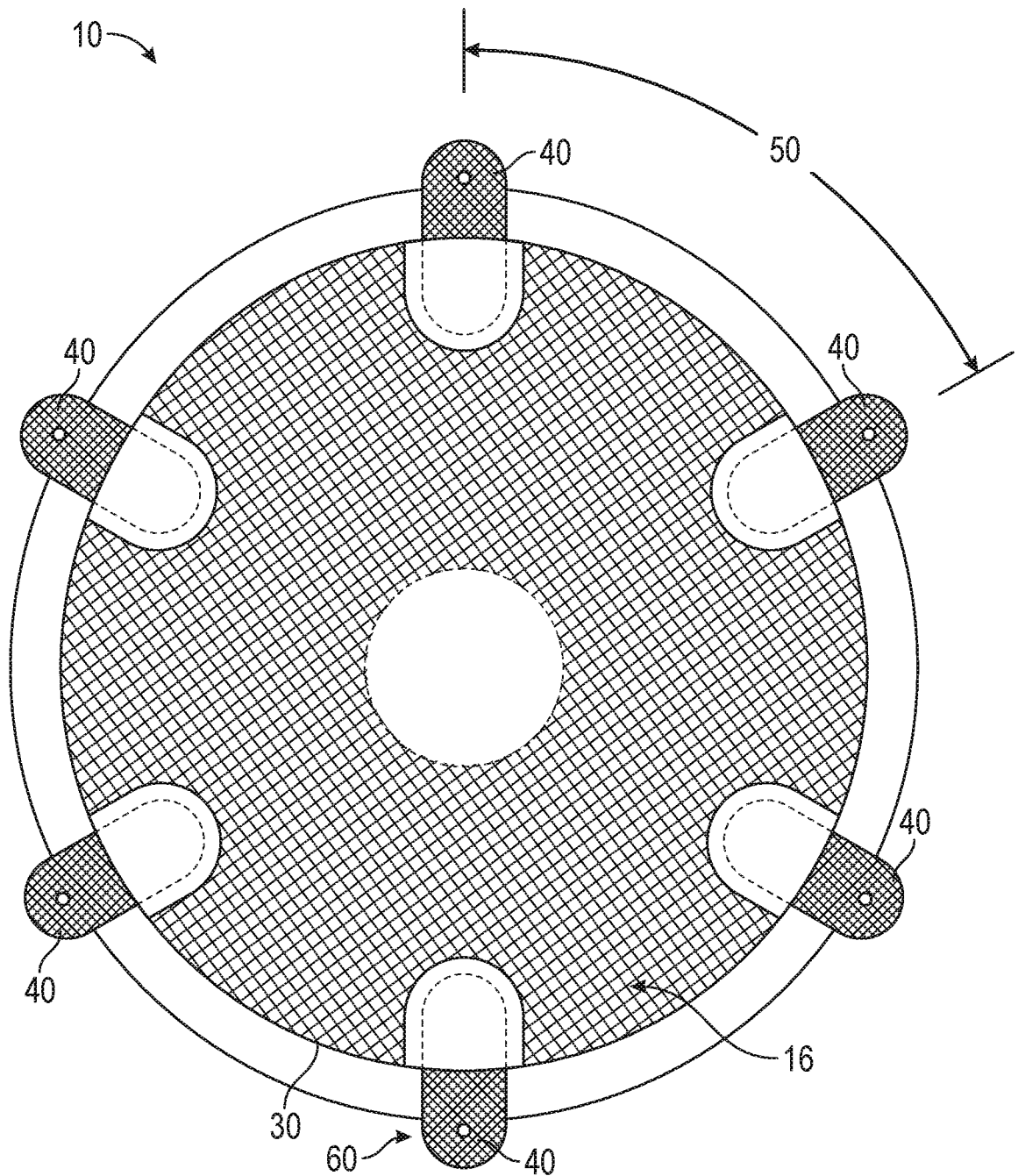
FIG. 3 is a rear plan view of the tissue expansion device of FIG. 1, according to some embodiments.

Referring to FIG. 3, the tabs 40 can be circumferentially spaced apart about the posterior portion of the shell 30. The tabs 40 can extend in radially outward direction relative to the center position 18 of the expandable shell 30. For example, if the device 10 uses six tabs, the tabs 40 can be circumferentially spaced apart at an angle 50 of approximately 60°. However, if the device uses two, three, four, five, seven, eight, nine, ten, eleven, twelve, or more tabs, the tabs can be spaced apart at an angle 50 that is based on or corresponds to the number of tabs. For example, in at least one embodiment, the tabs can be equally circumferentially spaced apart depending on the number of tabs (e.g., the tabs are circumferentially spaced apart at an angle equal to 360 degrees divided by the number of tabs), as in the embodiment illustrated in FIG. 3. Thus, in FIG. 3, the six tabs 40 are positioned circumferentially about the posterior portion of the shell at a 12 o'clock position, a 2 o'clock position, a 4 o'clock position, a 6 o'clock position, an 8 o'clock position, and a 10 o'clock position, respectively.

Additionally, in at least one embodiment, one or more of the tabs can comprise an attribute that is different from an attribute of one or more of the other tabs. The attribute may comprise at least one of a color of a tab, a size of a tab, a shape of the tab, or a material of a tab. One or more of the tabs can be differently colored or have a different shape, size, or material than the one or more of the other tabs. In at least one embodiment, one or more of the tabs can be white, tan, yellow, orange, red, pink, purple, blue, green, brown, gray, black, and/or any shades thereof.

For example, in at least one embodiment having six tabs, a 6 o'clock tab 60 can be white in color while the remainder of the tabs, positioned at 12 o'clock, 2 o'clock, 4 o'clock, 8 o'clock, and 10 o'clock positions, can be blue.

Further, in at least one embodiment, all of the tabs except for one may be white, while the other tab has a non-white color.

Furthermore, in at least one embodiment, one or more of the tabs can be a first color, one or more of the tabs can be a second color, or more of the tabs can be a third color, one or more the tabs can be a fourth color, one or more of the tabs can be a fifth color, and/or one or more of the tabs can be a sixth color.

As discussed further herein, the distinguishing attribute(s) of one or more tabs can help a clinician when placing the device 10 within the patient. For example, the tabs 40 can help a clinician to identify or discern the top portion 24, and/or bottom portion 26, and/or a lateral portions 28 of the device 10. For example, the clinician can recognize that the top portion 24 is adjacent the upper pole 20, the bottom portion 26 is adjacent the lower pole 22, and the lateral portions 28 are positioned between the top and bottom portions, which can assist the clinician in positioning or aligning the device 10, thereby ensuring that the shape of the device 10 is properly aligned relative to the patient's body. Further, as disclosed in more detail herein, certain attributes, such as the color, texture, or shape of the tabs can be modified or designed so as to help the clinician quickly identify the section or portion of the device 10 at which a given tab resides.

For example, in order to assist a clinician in identifying or discerning the top, bottom, and/or the alignment of the device 10, a plurality of tabs can be disposed about the top portion 24, the bottom portion 26, and/or the lateral portions 28 of the shell 30. In at least one embodiment, six tabs are spaced at 12 o'clock, 2 o'clock, 4 o'clock, 6 o'clock, 8 o'clock, and 10 o'clock positions, the tabs at the 4 o'clock, 6 o'clock, 8 o'clock positions can be a first color while the tabs at the 2 o'clock and 10 o'clock positions can be a second color. Optionally, the 12 o'clock tab can be either the first or second color. In such embodiments, the tabs at the 4 o'clock, 6 o'clock, and 8 o'clock positions can serve to indicate a top or bottom of the device 10. Further, in embodiments in which the 12 o'clock tab is the first color (the same color as the tabs at the 4 o'clock, 6 o'clock, and 8 o'clock positions), the clinician may be able to easily discern both the top and bottom of the device 10, as well as the alignment of the device 10. Additionally, in at least one embodiment, the color scheme may vary such that the tabs at the 4 o'clock and 8 o'clock positions have a different color than the remainder of the tabs.

Optionally, the tissue expansion device 10 can also comprise an orientation indicator 70. As noted above, the present disclosure notes the realization that if anatomically shaped, breast implants are generally symmetrical about a centerline and therefore, require the surgeon to be aware of that centerline so the device is implanted in the proper orientation. Although certain tissue expansion devices have previously incorporated raised silicone dots on the surface of the shell to provide palpable and visual indicators or visible lines on the shell of contrasting color, such as blue or white, to indicate the centerline, these dots or lines are applied to the implant shell during secondary assembly operations. Thus, the cost for manufacturing is high and the additional material or color can be lost or may be inaccurately applied. As such, in addition to the challenge of properly aligning the tissue expansion device or breast implant relative to the patient's anatomy, the manufacturing process that creates indicator dots and lines may be inadequate or inaccurate, which inaccuracies can be difficult for the clinician to appreciate or overcome. In contrast, the present disclosure provides a solution that creates an orientation indicator 70 that is formed with and/or along an inner surface of the shell 30, thereby avoiding the additional manufacturing costs and ensuring that the orientation indicator 70 is accurately placed relative to the shell 30 and its shape.

In at least one embodiment, the orientation indicator 70 is visible along the anterior portion 14 of the shell 30. The orientation indicator 70 can be disposed along the lower pole 22 of the shell 30. However, the orientation indicator 70 can also extend along the upper pole 20 of the shell 30. Further, in some embodiments, the orientation indicator 70 can extend along both the upper pole 20 and the lower pole 22.

The orientation indicator 70 can extend to and/or beyond the center position 18 of the shell 30. Further, the orientation indicator 70 can extend through and beyond, through, or only up to the injection port 12.

As shown in FIG. 2, the orientation indicator 70 can extend as a vertical line along a vertical dimension. However, the orientation indicator 70 can also extend as a generally horizontal line along a horizontal dimension. The longitudinal extent of the orientation indicator 70 can correspond to a vertical or horizontal dimension. For example, referring to the front view of FIG. 2, the orientation indicator 70 can extend from the lower portion 26, upwardly across at least 50% of the diameter or height of the expandable shell 30. In accordance with some embodiments, the orientation indicator 70 can extend up to about 50%, at least about 50%, at least about 55%, at least about 60%, at least about 65%, at least about 70%, at least about 75%, at least about 80%, at least about 85%, at least about 90%, at least about 95%, or up to the entirety of a given dimension, diameter, or height of the expandable shell 30. The width, patterning, shape, and/or longitudinal extent of the orientation indicator 70 can advantageously be designed to provide a ready visual tool for placing and aligning the device 10. This dedicated feature provide unique, cost-effective advantages from both manufacturing and clinical perspectives.

The orientation indicator 70 can provide one or more geometric patterns or shapes that can allow the clinician to identify an aspect of and/or the orientation of the tissue expansion device 10 during implantation of the device 10 within a cavity of a patient. As illustrated in FIG. 2, the orientation indicator 70 can comprise a band, strip, or line that extends along and is visible along the shell 30. Further, the orientation indicator 70 can be aligned with one or more components or aspects of the tissue expansion device 10. For example, the orientation indicator 70 can be aligned with at least one of the plurality of tabs 40. If a line or linear pattern, the orientation indicator 70 can extend along a vertical, horizontal, or other axis. The visual perception of the orientation indicator 70 can enable a clinician to adjust a position of the tissue expansion device 10 within the cavity by aligning the orientation indicator 70 relative to a horizontal or vertical plane or other indicia.

Although various configurations can be created, the embodiment shown in FIG. 2 illustrates that the orientation indicator 70 extends along a generally vertical plane between an edge of the shell 30 adjacent to the 6 o'clock tab 60 and the injection port 12. The orientation indicator 70 can extend partially or fully along such a path, along the lower pole 22 of the shell 30. Optionally, the orientation indicator 70 can extend along the upper pole 20 along the same vertical plane. However, the embodiment illustrated in FIG. 2 advantageously provides a clear indication to the clinician as to the orientation of the tissue expansion device 10 because it appears in only the lower pole 22 and also provides a sufficiently long line as a visual indicator.

In some embodiments, the orientation indicator 70 comprises a line having a first end portion 72 adjacent to an edge of the shell 30 and a second end portion 74 distal to the edge of the shell. The injection port 12 can intersect with the second end portion of the orientation indicator 70. Optionally, the second end portion 74 of the orientation indicator extends to or is aligned with an outer perimeter 13 of the injection port 12.

In accordance with some embodiments, advantageously, in addition to facilitating alignment and proper placement of the device within a patient, the orientation indicator 70 can also be used to facilitate manufacturing of the device 10. For example, the orientation indicator 70 can be used to increase the manufacturing efficiency and accuracy of each device 10, as well as the manufacturing consistency between multiple devices 10. For example, after the shell 30 is manufactured with the orientation indicator 70, the injection port 12 can be positioned along the shell 30 by aligning a portion of the injection port 12 with a portion of orientation indicator 70. For example, the outer perimeter 13 (e.g., a lowermost portion of the perimeter or a central portion) of the injection port 12 can be placed so as to abut or otherwise be aligned with the second end portion 74 of the orientation indicator.

Figure 4A:
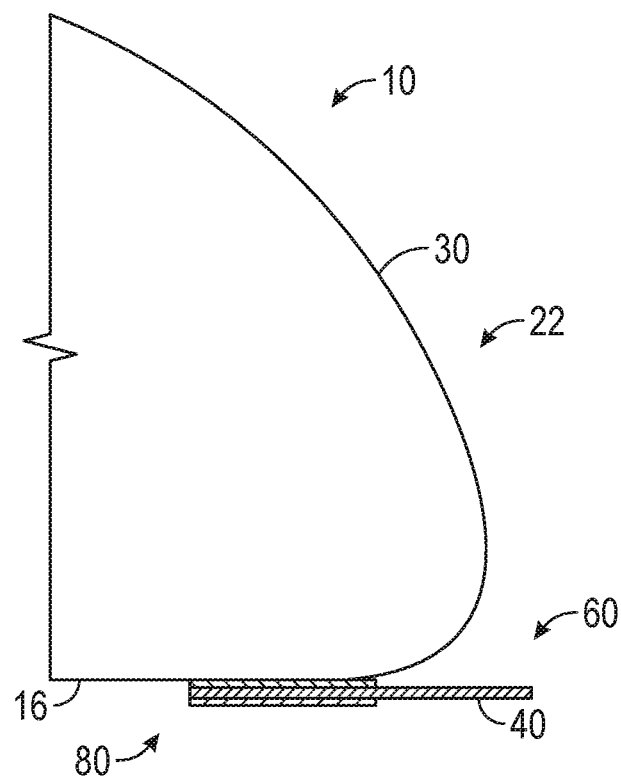
FIG. 4A is a partial side view of the tissue expansion device of FIG. 1, according to some embodiments.
Figure 4B:
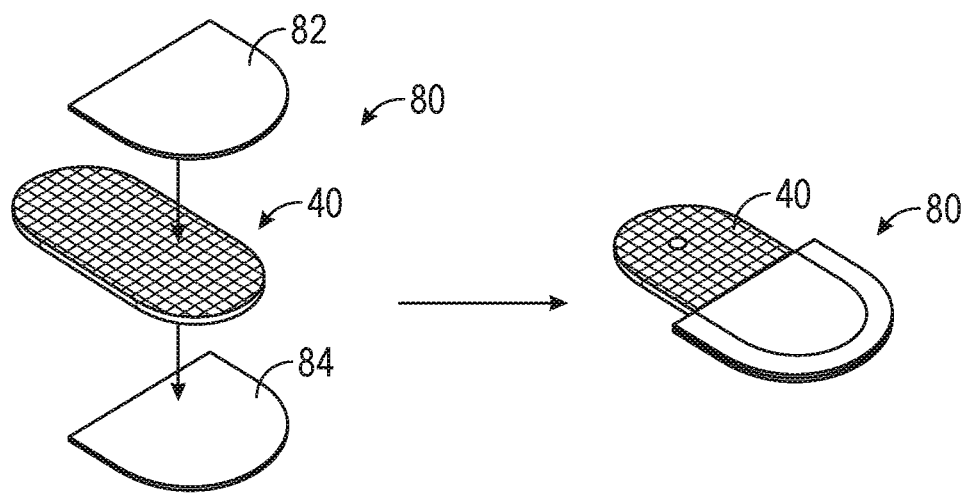
FIG. 4B is an exploded and assembled view of a tab and engagement assembly of the tissue expansion device of FIG. 1, according to some embodiments.

Referring now to FIGS. 3-4B, the tabs 40 can be coupled to the shell 30 by an adhesive or co-molded with a portion of the shell 30. FIGS. 4A and 4B illustrate a side view and perspective assembly views of a tab 40. FIG. 4A illustrates the 6 o'clock tab 60 and its engagement structure 80 in side view. FIG. 4B illustrates an exploded view and an assembly view of the engagement structure 80 with the tab 40. The engagement structure 80 can comprise upper and lower engagement layers 82, 84 that sandwich the tab 40 therebetween. The engagement structure 80 and the tab 40 can be attached to the shell 30 and vulcanized. The tabs 40 can comprise a surface structure or mesh pattern along an outer surface thereof, which can assist in grasping the tab 40 in order to manipulate a position of the device 10 and two further enhance engagement with the upper and lower engagement layers 82, 84. As shown in FIG. 4A, the engagement structure 80 and the tab 40 can be coupled to the posterior portion 16 of the shell 30.

Figure 5:
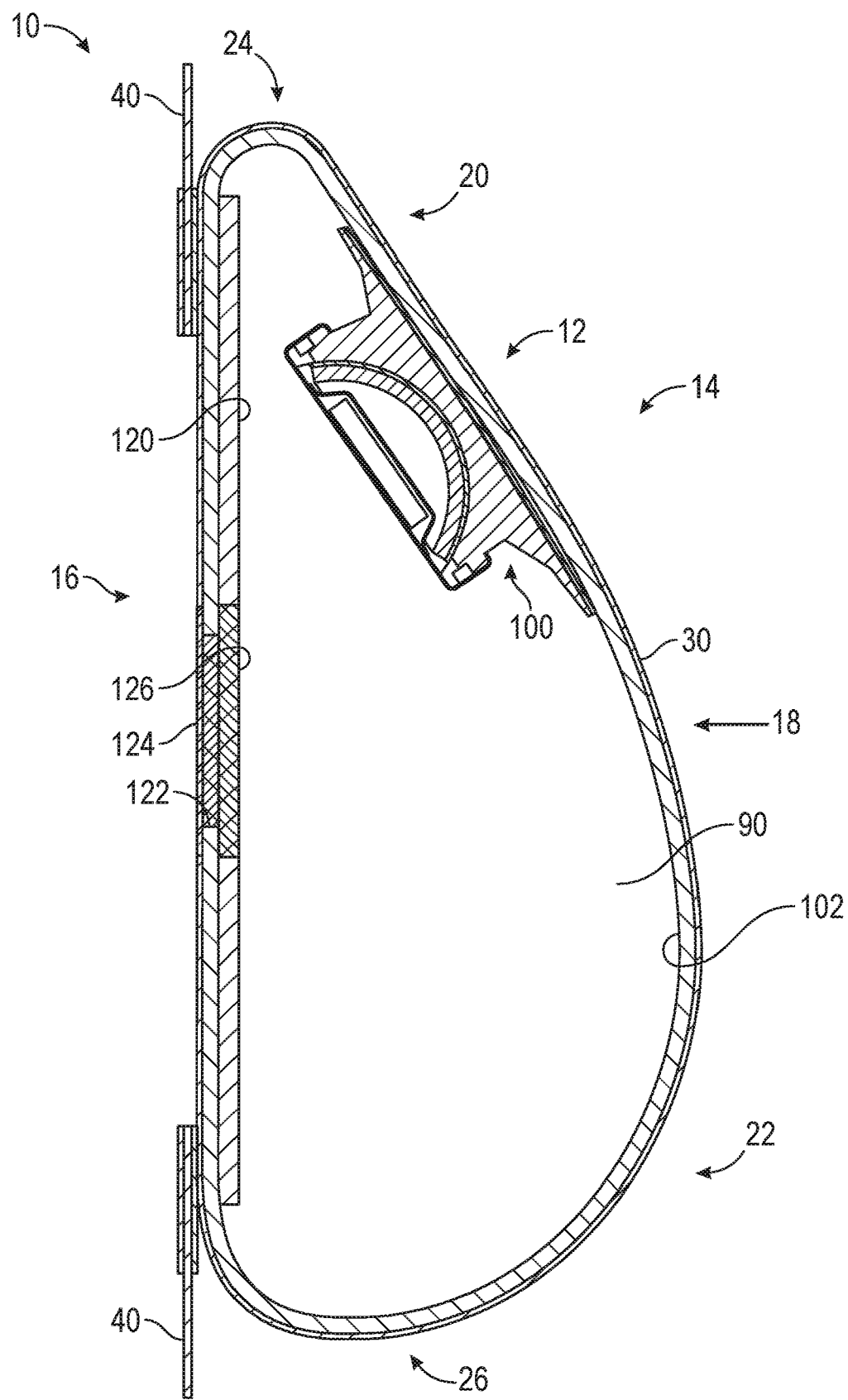
FIG. 5 is a cross-sectional side view of the tissue expansion device of FIG. 1 taken along section lines 5-5, according to some embodiments.
Figure 6:
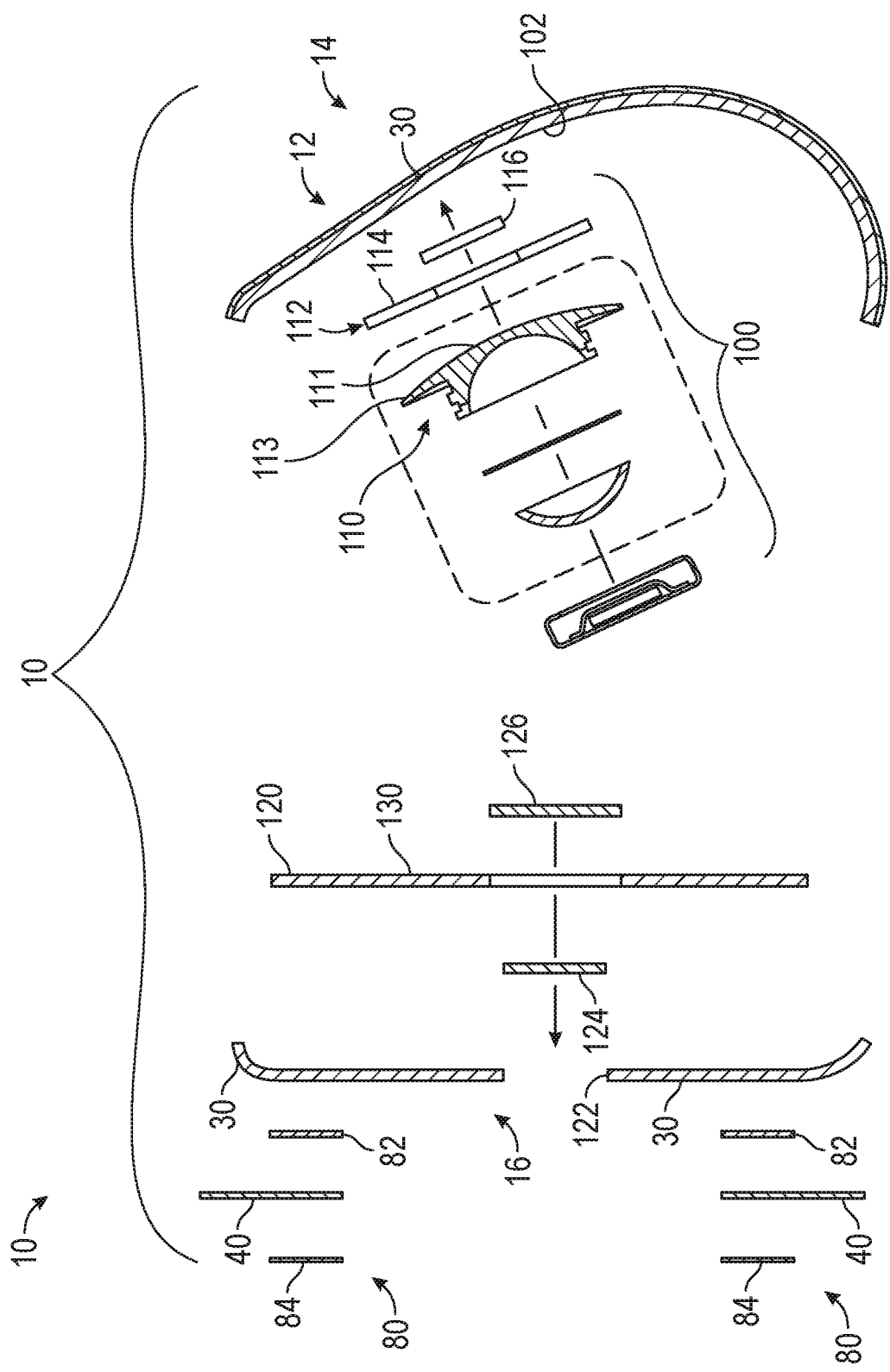
FIG. 6 is an exploded view of the tissue expansion device of FIG. 1, according to some embodiments.

FIGS. 5 and 6 illustrate side cross-sectional views of the tissue expansion device 10 in an assembled and an exploded state, respectively. As shown in FIG. 5, the injection port 12 of the device 10 be positioned within a cavity 90 of the shell 30. The injection port 12 can comprise an injection reservoir assembly 100 that is coupled to an inner surface 102 of the shell 30. The injection reservoir assembly 100 can be fabricated similar to that disclosed in U.S. Pat. No. 4,671,255, which is owned by the present applicant, the entirety of which is incorporated herein by reference.

In the present disclosure, the injection reservoir assembly 100 can comprise an injection reservoir 110 that is coupled to or laminated onto the inner surface 102 of the shell 30. The injection reservoir assembly 100 can provide a self-sealing valve or injection port that will tend to seal any puncture or opening created by a needle when it is advanced into and later withdrawn from the injection port 12.

FIG. 5 shows the upper pole 20 positioned between the center position 18 of the shell 30 and a top edge of the shell 30 at the top portion 24, and the lower pole 22 positioned between the center position 18 of the shell 30 and a bottom edge of the shell 30 at the bottom portion 26. The injection port 12 can be positioned entirely within the upper pole 20. In some embodiments, however, only a portion of the injection port 12 can be positioned within the upper pole 20, with a portion of the injection port 12 extending across the center position 18. In some embodiments, at least 50% of the injection port 12 is positioned within the upper pole 20.

The orientation indicator 70 can extend from the injection port 12 toward the bottom edge of the shell 30, as shown in the front view of the device 10 in FIG. 2. Further, in some embodiments, the orientation indicator 70 can extend from the injection port 12 toward another edge of the shell 30, such as the top edge or a lateral edge of the shell 30. Additionally, in some embodiments, the orientation indicator 70 can extend from the injection port 12 across a portion of the upper pole 20 and across the lower pole 22.

As shown in FIG. 6, the injection reservoir 110 can be coupled to the inner surface 102 via a coupling layer 112. In at least one embodiment, the coupling layer 112 can comprise a reinforced ring 114 and a filler plug 116. The reinforced ring 114 can comprise a mesh or fabric material that is co-molded with a polymer, such as silicone. The reinforced ring 114 can serve to increase the durability of the injection reservoir assembly 100. The reinforced ring 114 can optionally be configured as a tear-resistant layer.

The injection reservoir 110 can include reservoir body 111 and a flange 113 that extends radially outward from the reservoir body 111. The flange 113 can comprise a thickness that tapers away from the reservoir body 111. The reservoir body 111 can form an intermediate perimeter of the injection reservoir 110, while the flange 113 can form or extend along the outer perimeter 13 of the injection port. When the orientation indicator 70 is used as a reference point during manufacturing, e.g., to position the injection port 12, the flange 113 can be positioned to align with the second end portion 74 of the orientation indicator when coupling the injection reservoir 110 to the device 10.

The tapered flange 113 can provide a flexible (or alternatively, a more rigid) portion of the injection reservoir 110. For example, the flange 113 can flex, relative to the reservoir body 111, thereby providing a smooth, less abrupt transition between the injection reservoir 110 and the adjacent portion of the device 10. Thus, when a force (such as a bending force or a point stress exerted against the shell 30) is directed against the injection reservoir 110 or adjacent area thereto, the flange 113 can tend to flex or provide a rigid, tactilely discernible perimeter for the injection port 12. Additionally, the flange 113 provide an increased surface area, relative to the reservoir body 111, to couple the injection reservoir 110 to the inner surface 102 of the shell, thereby advantageously ensuring a greater seal between the injection reservoir 110 and the inner surface 102. Thus, the material, structure, and radial extent of the flange 113 can be selected so as to provide a desired amount of surface area and a desired structural behavior for the injection port 12.

The tissue expansion device 10 can also comprise a stable base 120 that is coupled to the inner surface 102 of the shell 30 along the posterior portion 16 of the shell. As shown, the shell 30 can comprise a mandrel aperture 122 that extends through the posterior portion of the shell 30. The stable base 120 can be coupled to the posterior portion 16 and provide structural support thereto, especially around the mandrel aperture 122. Additionally, the tissue expansion device can comprise a filler plug 124 and a patch 126 that can be used to fill and seal the mandrel aperture 122.

In accordance with at least one embodiment, as noted previously, the shell 30 can comprise an opaque or translucent appearance. In order to achieve the opaque or translucent appearance, the shell 30 can be fabricated such that the inner surface 102 comprises a roughened texture. Thus, light passing through the shell 30 will be diffracted and the passage of light will be impeded, thus achieving an opaque or translucent appearance of the shell 30.

In accordance with a realization of at least one embodiment disclosed herein, when the stable base 120 is coupled to or laminated against the inner surface 102 of the shell 30, many of the microscopic gaps and pockets of the roughened texture of the inner surface 102 will be filled in with and eliminated by material from the stable base 120 as a result of the lamination process. As the roughened texture of the inner surface 102 is eliminated through the lamination process, light diffraction will be greatly reduced, thus creating a clear or transparent appearance along these areas of coupling between the stable base 120 with the shell 30. In some cases, the now-clear or transparent appearance along these areas can tend to draw attention to any air pockets, striations, fractures, or other imperfections of the lamination between these components. Although a similar result may be detected in the lamination between the injection reservoir assembly 110 and the inner surface 102 of the shell 30, the reinforced ring 114 may be configured to include a mesh pattern that can tend to mask or disguise any visual imperfections in the lamination process.

To provide an attractive appearance and disguise any visual imperfections in the lamination between the stable base 120 and the inner surface 102 of the shell 30, at least one embodiment can be configured such that the stable base 120 comprises a textured inner surface 130. The textured inner surface 130 can provide a visually similar appearance to the mesh pattern of the reinforced ring 114. Because the laminated stable base 120 and inner surface 102 will provide a generally transparent view of the textured inner surface 130, the tissue expansion device can be provided with a consistent pattern along the injection port 12 in the anterior portion 14 of the device 10, the posterior portion 16, and the tabs 40. Further, although the pattern in the illustrated embodiment is discussed as being a mesh pattern, other patterns can provided. Further, the pattern of the textured inner surface 130 can also be selected to be distinct from the pattern provided by the reinforced ring 114 at the injection port 12 and/or the tabs 40.

The shell 30 has a thickness extending between the outer surface and the inner surface 102 of the shell. The thickness of the shell can be approximately constant along each of the anterior portion 14 and the posterior portion 16 of the device. The constant thickness of the shell 30 can provide consistent light penetration and/or diffraction through the shell 30, and can provide consistent resistance along all portions of the shell 30. However, in some embodiments, the thickness of the shell 30 can increase and/or decrease along any portion thereof. For example, the thickness of the shell 30 can decrease from the anterior portion 14 toward the posterior portion 16. In some embodiments, the thickness of the shell 30 can decrease from the lower pole 22 toward the upper pole 20. Such variations in thickness can advantageously provide desired tactile feedback to assist the clinician in aligning the device 10 relative to the anatomy of the patient.

When viewed in cross-section, such as shown in FIG. 5, the device 10 has a width extending between the posterior portion 16 and the anterior portion 14. The width of the device 10 tapers from the lower pole 22 toward the upper pole 20. In some embodiments, when moving from the bottom portion 26 toward the top portion 24, the width of the device 10 increases along the lower pole 22, and then the width of the device 10 decreases along the upper pole 20. In some embodiments, the device 10 has a maximum width at the lower pole 22, proximal to the center position 18, and a minimum width at the upper pole 20, adjacent to the top portion 24.

In accordance with some embodiments, the outer surface of the shell 30 along the anterior portion 14, can comprise a generally convex shape. However, it should be understood that a portion of the shell 30 can have a convex shape or a concave shape. For example, the outer surface of the shell 30 along a portion of the lower pole 22 can be convex, while the outer surface of the shell 30 along a portion of the upper pole 20 can be concave. In some embodiments, the outer surface of the shell 30 transitions from a convex shape to a concave shape along a portion of the upper pole 20.

Figure 7A:
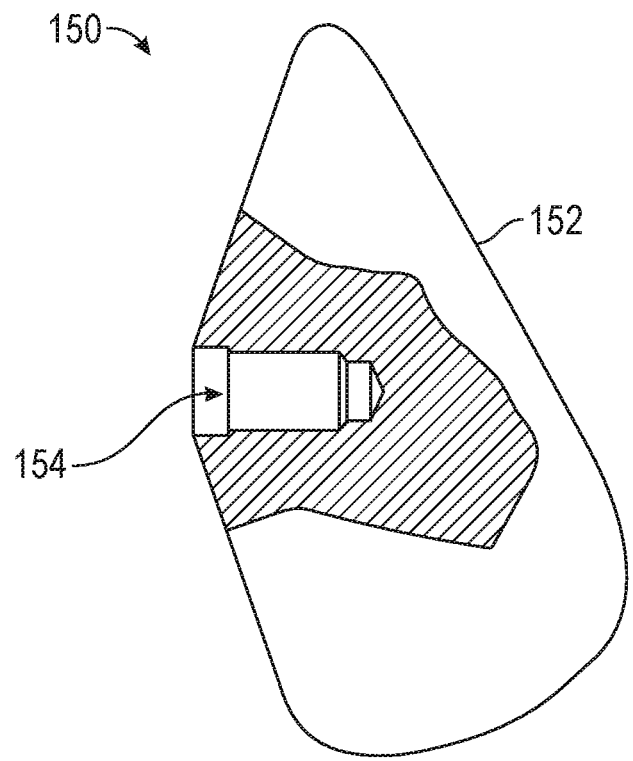
FIG. 7A is a side view of a mandrel for manufacturing a tissue expansion device, according to some embodiments.
Figure 7B:
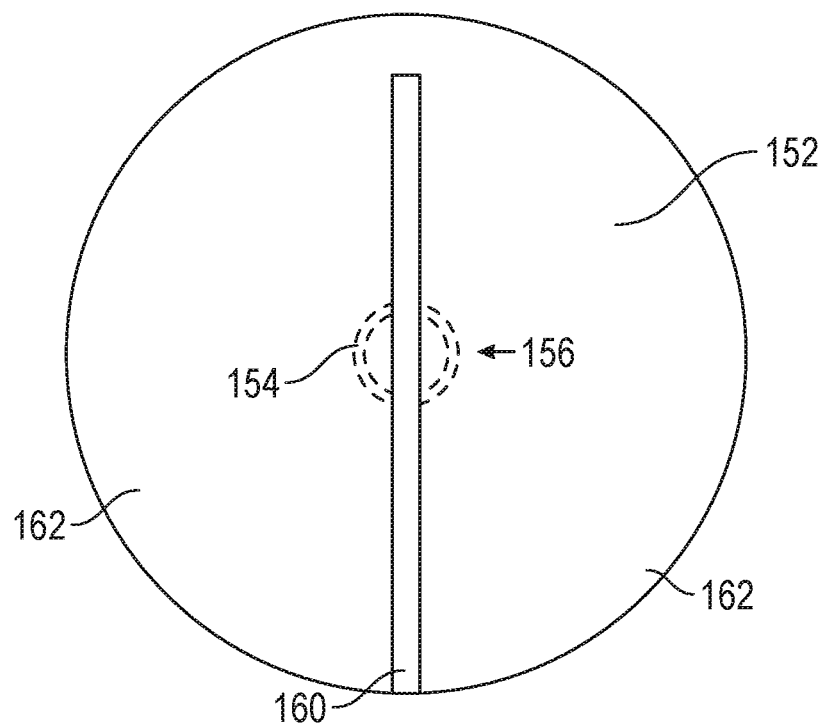
FIG. 7B is a front view of the mandrel of FIG. 7A, according to some embodiments.

Referring now to FIGS. 7A and 7B, a mandrel 150 is illustrated that can be used in fabricating at least one embodiment disclosed herein. The casting tool or mandrel 150 can comprise an outer surface 152. During manufacturing of the device 10, the mandrel 150 can be coupled to another tool or support apparatus using a coupling recess 154 of the mandrel. In some embodiments, the coupling recess 154 is positioned at the center 156 of the mandrel. The coupling recess 154 can correspond to the mandrel aperture 122 of a shell, and the center 156 of the mandrel can correspond to the center position 18 of a shell, such as the shell 30 discussed in the embodiment of FIGS. 1-6.

As shown in front view of the mandrel 150 in FIG. 7B, the outer surface 152 can have a smooth region 160 and a roughened region 162. The smooth region 160 can correspond to an orientation indicator, such as the orientation indicator 70 discussed in the embodiment of FIGS. 1-6. In some embodiments, a roughened region of the outer surface 152 can correspond to an orientation indicator, and another portion of the outer surface 152 can have a smooth region. FIG. 7B also demonstrates how the smooth region 160, which can correspond to an orientation indicator, extends across the center 156 of the mandrel, which can correspond to a center position 18 of a shell.

In accordance with at least one method of manufacturing the tissue expansion device 10, the mandrel 150 can be dipped into a polymer solution and subsequently dried, which can produce a shell. The shell will have a shape consistent with the shape of the outer surface 152 of the mandrel 150. However, in addition, the shell can have an inner surface that corresponds to the smooth region 160 and the roughened region 162 of the outer surface 152 of the mandrel 150. In this manner, a desired texture of the inner surface 102 of the shell 30 discussed above, as well as any shape or pattern of the orientation indicator 70, can be achieved. In this manner, various advantages can be achieved over prior devices and methods of manufacture.

Figure 8:
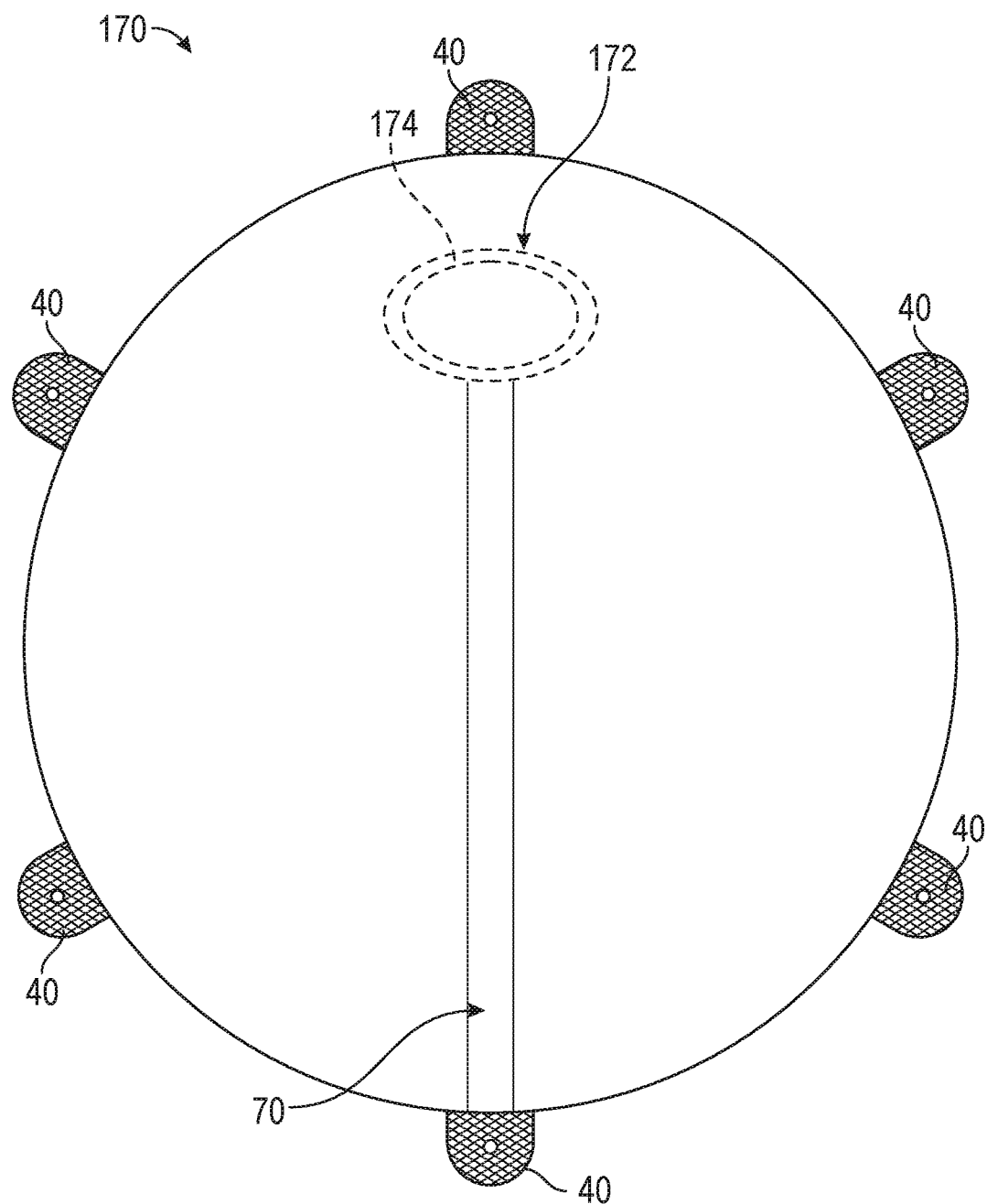
FIG. 8 is a front view of an alternative embodiment of a tissue expansion device, according to some embodiments.
Figure 9:
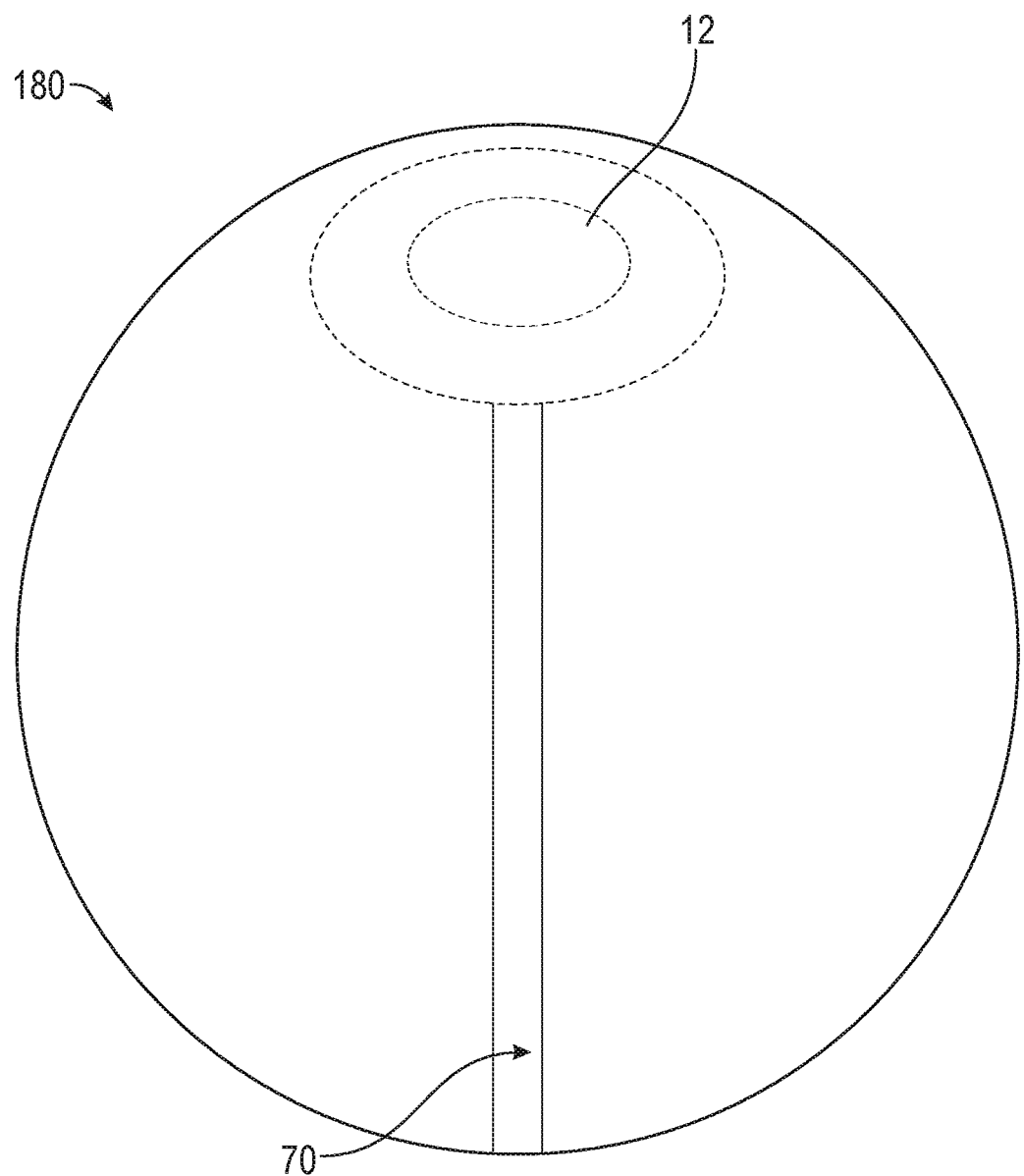
FIG. 9 is a front view of an alternative embodiment of a tissue expansion device, according to some embodiments.
Figure 10:
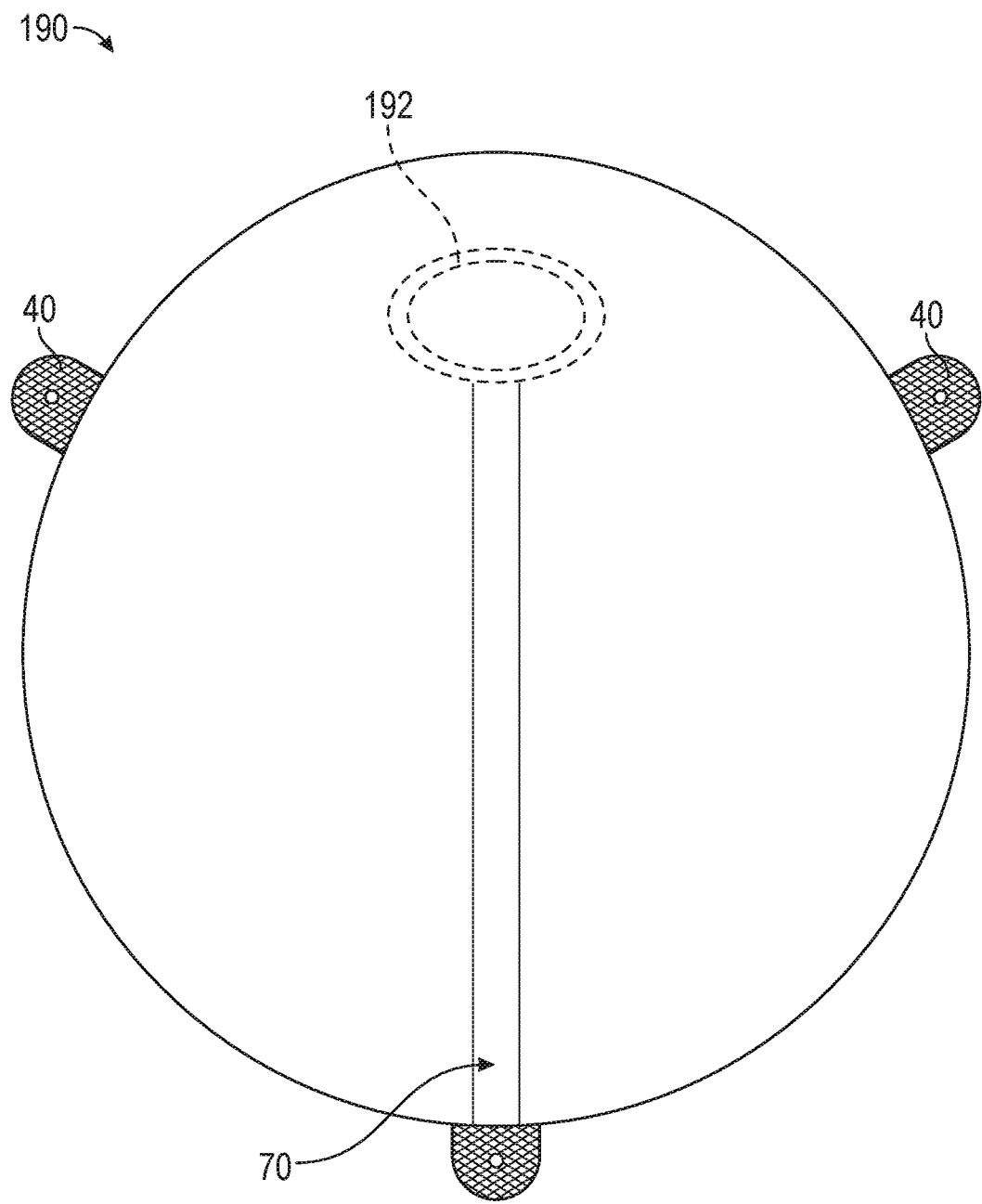
FIG. 10 is a front view of an alternative embodiment of a tissue expansion device, according to some embodiments.

FIGS. 8, 9, and 10 illustrate different embodiments of the tissue expansion device 10. For example, FIG. 8 illustrates an embodiment of a tissue expansion device 170 that comprises a plurality of tabs 40, an orientation indicator 70, and other such features similar to the tissue expansion device 10, details of which will not be discussed herein for brevity, but are incorporated by reference from the disclosure above. However, the device 170 can be configured to comprise an injection port 172 having a visible or tactile outer ring 174. The injection port 172 can be compact and have a coupling area along the outer ring 174 that is smaller in size than that of the injection port 12.

Referring to FIG. 9, in embodiment of a tissue expansion device 180 is illustrated in which the device 180 does not comprise tabs. Features of the device 180 can be similar to those discussed above with respect to the device 10 and are not discussed herein for brevity, but are incorporated by reference from the disclosure above. However, the device 180 can be manufactured and used without the tabs disclosed above with respect to the device 10. Further, although the device 180 can be configured without any tabs, other embodiments can be configured to include one or more tabs, as disclosed herein.

For example, FIG. 10 illustrates an embodiment of a tissue expansion device 190 that comprises three tabs that are circumferentially offset at 120° from each other. Features of the device 190 can be similar to those discussed above with respect to the device 10 and are not discussed herein for brevity, but are incorporated by reference from the disclosure above. Further, the injection port 192 can form a transparent or opaque, nonwhite portion of the device 190 without any underlying pattern from a reinforced ring. Further, the device 190 can be configured to comprise a corresponding or different appearance of the posterior portion and/or tabs of the device relative to the injection port 192.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A tissue expansion device for temporary surgical implantation beneath skin of a patient and for removal upon predetermined expansion of overlying tissue, the device comprising: an expandable shell forming an expandable chamber, the shell having an anterior portion and a posterior portion; an orientation indicator visible along the anterior portion of the expandable shell, wherein, when the expandable shell expandable shell is viewed from the front, the orientation indicator extends across at least 50% of a vertical dimension of the expandable shell; and an injection port, coupled to the anterior portion of the shell, in fluid communication with the chamber and configured to permit injection of fluid into the chamber from a hypodermic needle.

Clause 2. The device of Clause 1, further comprising a plurality of tabs coupled to the posterior portion of the shell.

Clause 3. The device of Clause 1, further comprising a plurality of tabs disposed about top, bottom, and lateral portions of the expandable shell.

Clause 4. The device of Clause 2, wherein each of the plurality of tabs extends in radially outward direction relative to a center position of the device.

Clause 5. The device of any one of Clauses 2-4, wherein the plurality of tabs comprises six tabs.

Clause 6. The device of any one of Clauses 2-5, wherein the plurality of tabs comprises six tabs, and wherein the six tabs are positioned circumferentially about the posterior portion of the shell at a 12 o'clock position, a 2 o'clock position, a 4 o'clock position, a 6 o'clock position, an 8 o'clock position, and a 10 o'clock position, respectively.

Clause 7. The device of any one of Clauses 2-6, wherein at least one of the plurality of tabs comprises an attribute different from an attribute of a remainder of the plurality of tabs.

Clause 8. The device of Clause 7, wherein the attribute comprises at least one of a color of the tab, a size of the tab, a shape of the tab, or a material of the tab.

Clause 9. The device of any one of Clauses 2-8, wherein the plurality of tabs comprises six tabs, and wherein a first of the six tabs has a first color and a remainder of the six tabs has a second color.

Clause 10. The device of Clause 9, wherein the first of the six tabs is positioned at a bottom portion of the expandable shell.

Clause 11. The device of any one of Clauses 2-10, wherein each of the plurality of tabs comprises an aperture for receiving a suture therethrough.

Clause 12. The device of any one of Clauses 1-11, wherein the orientation indicator is formed along an inner surface of the shell.

Clause 13. The device of any one of Clauses 1-12, wherein the orientation indicator comprises a line.

Clause 14. The device of any one of Clauses 1-13, wherein the orientation indicator comprises a line extending from the injection port toward an edge of the shell.

Clause 15. The device of any one of Clauses 1-14, wherein the orientation indicator extends across at least about 50% of a dimension of the expandable shell.

Clause 16. The device of any one of Clauses 1-15, wherein the orientation indicator extends across at least about 55% of a dimension of the expandable shell.

Clause 17. The device of any one of Clauses 1-16, wherein the orientation indicator extends across at least about 60% of a dimension of the expandable shell.

Clause 18. The device of any one of Clauses 1-17, wherein the orientation indicator extends across at least about 65% of a dimension of the expandable shell.

Clause 19. The device of any one of Clauses 1-18, wherein the orientation indicator extends across at least about 70% of a dimension of the expandable shell.

Clause 20. The device of any one of Clauses 1-19, wherein the orientation indicator extends across at least about 75% of a dimension of the expandable shell.

Clause 21. The device of any one of Clauses 1-17, wherein the orientation indicator extends across a center position of the expandable shell.

Clause 22. The device of any one of Clauses 1-14, wherein the orientation indicator extends across at least about 50% of a vertical dimension of the expandable shell.

Clause 23. The device of Clause 1, further comprising a plurality of tabs coupled to the posterior portion of the shell, wherein a first tab of the plurality of tabs is coupled to the shell at a 6 o'clock position, and wherein the orientation line extends from the injection port toward the first tab at the 6 o'clock position.

Clause 24. The device of Clause 1, further comprising a plurality of tabs coupled to the posterior portion of the shell, wherein the orientation indicator is aligned with at least one of the plurality of tabs.

Clause 25. The device of any one of Clauses 1-24, wherein the orientation indicator comprises a surface texture of the expandable shell.

Clause 26. The device of any one of Clauses 1-25, wherein the orientation indicator comprises a surface texture of an interior surface of the expandable shell.

Clause 27. The device of any one of Clauses 1-26, wherein an exterior surface of the expandable shell comprises a smooth finish, the orientation indicator comprises a smooth finish on an interior surface of the expandable shell, and a remainder of the interior surface of the expandable shell comprises a roughened finish.

Clause 28. The device of any one of Clauses 1-27, wherein the orientation indicator comprises a line having a first end portion adjacent to an edge of the shell and a second end portion distal to the edge of the shell, and wherein the second end portion intersects the injection port.

Clause 29. The device of Clause 28, wherein the second end portion of the orientation indicator is aligned with an outer perimeter of the injection port.

Clause 30. The device of any one of Clauses 1-29, wherein the orientation indicator is a transparent portion of the shell.

Clause 31. The device of any of the preceding Clauses, wherein an outer surface of the shell comprises a smooth finish.

Clause 32. A method of implanting the tissue expansion device of any of the preceding Clauses, the method comprising: positioning the tissue expansion device within a cavity of a patient; and adjusting a position of the tissue expansion device within the cavity by aligning an orientation indicator relative to a horizontal or vertical plane.

Clause 33. The method of Clause 32, wherein the orientation indicator comprises a transparent portion of the shell of the tissue expansion device, and the adjusting comprises aligning the orientation indicator relative to a vertical plane.

Clause 34. The method of Clause 33, wherein tissue expansion device comprises a plurality of tabs coupled to a posterior portion thereof, and wherein the orientation indicator is aligned with a first tab of the plurality of tabs located at a 6 o'clock position, and the adjusting comprises aligning the orientation indicator and the first tab relative to a vertical plane.

Clause 35. A method of manufacturing a tissue expansion device, the method comprising: dipping a casting tool into a polymer solution to form a shell along an outer surface of the casting tool, the casting tool outer surface having a textured portion and a smooth portion; permitting the shell to dry; and removing the shell from the casting tool, the shell having an inner surface comprising a first portion corresponding to the textured portion and a second portion corresponding to the smooth portion, the shell having a smooth outer surface, wherein the smooth outer surface of the shell and the second portion collectively define a transparent orientation indicator, and wherein the smooth outer surface of the shell and the first portion of the shell inner surface collectively define a translucent or opaque section of the shell that visually contrasts against the transparent orientation indicator, wherein the orientation indicator extends across at least 50% of a diameter of the expandable shell.

Clause 36. The method of Clause 35, further comprising coupling a plurality of tabs to a posterior portion of the shell.

Clause 37. The method of Clause 36, wherein the coupling comprises coupling the plurality of tabs circumferentially about the posterior portion of the shell at a 12 o'clock position, a 2 o'clock position, a 4 o'clock position, a 6 o'clock position, an 8 o'clock position, and a 10 o'clock position, respectively.

Clause 38. The method of Clause 37, wherein a first tab of the plurality of tabs comprises an attribute different from an attribute of a remainder of the plurality of tabs, and wherein the method further comprises positioning the first tab at a 6 o'clock position on the posterior portion of the shell.

Clause 39. The method of Clause 38, wherein the attribute comprises at least one of a color of the tab, a size of the tab, a shape of the tab, or a material of the tab.

Clause 40. The method of any of Clauses 35-39, further comprising coupling an injection reservoir assembly to the shell inner surface at an injection port section of the shell inner surface to change the translucent or opaque section to transparent along the injection port section.

Clause 41. The method of Clause 40, wherein the injection reservoir assembly comprises a reinforced ring having a first pattern formed therein, the first pattern being visible through the transparent injection port section when the injection reservoir assembly is coupled to the shell.

Clause 42. The method of Clause 41, wherein the first pattern comprises a mesh pattern.

Clause 43. The method of any of Clauses 35-42, further comprising coupling a stable base to the shell inner surface along a posterior portion of the shell to change the translucent or opaque section to transparent along a section of the posterior portion.

Clause 44. The method of Clause 43, wherein the stable base comprises a patterned internal surface having a second pattern formed therein, the second pattern being visible through the transparent section of the posterior portion when the stable base is coupled to the shell.

Clause 45. The method of Clause 44, wherein the second pattern comprises a mesh pattern.

Clause 46. The method of any of Clauses 35-45, further comprising coupling an injection reservoir assembly to the shell inner surface at an injection port section of the shell, wherein coupling the injection reservoir assembly comprises aligning an outer perimeter of the injection reservoir with an end portion of the orientation indicator.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A tissue expansion device for temporary surgical implantation beneath skin of a patient and for removal upon predetermined expansion of overlying tissue, the device comprising:
    an expandable shell forming an expandable chamber, the shell having an anterior portion, a posterior portion, and a smooth interior surface;
    an orientation indicator formed along an interior surface of the expandable shell and visible along the anterior portion of the expandable shell, wherein, the orientation indicator comprises a textured vertical strip adjacent to the smooth interior surface of the expandable shell, and when the expandable shell is seen in front view, the orientation indicator extending across at least 50% of a vertical dimension of the expandable shell; and
    an injection port, coupled to the anterior portion of the shell, in fluid communication with the chamber and configured to permit injection of fluid into the chamber from a hypodermic needle.

2. The device of claim 1, further comprising a plurality of tabs coupled to the posterior portion of the shell.

3. The device of claim 2, wherein at least one of the plurality of tabs comprises an attribute different from an attribute of a remainder of the plurality of tabs.

4. The device of claim 3, wherein the attribute consists of at least one of a color of the tab, a size of the tab, a shape of the tab, or a material of the tab.

5. The device of claim 2, wherein a first of the plurality of tabs is positioned at a bottom portion of the expandable shell.

6. The device of claim 1, wherein the orientation indicator extends more than 50% of the vertical dimension of the expandable shell.

7. The device of claim 1, wherein the orientation indicator extends across a center position of the expandable shell.

8. The device of claim 1, further comprising a plurality of tabs coupled to the posterior portion of the shell, wherein the orientation indicator is aligned with at least one of the plurality of tabs.

9. The device of claim 1, wherein the orientation indicator comprises a surface texture of the expandable shell.

10. The device of claim 1, wherein the orientation indicator comprises a line having a first end portion adjacent to an edge of the shell and a second end portion distal to the edge of the shell, and wherein the second end portion intersects the injection port.

11. A method of implanting the tissue expansion device of claim 1, the method comprising:
    positioning the tissue expansion device within a cavity of a patient; and
    adjusting a position of the tissue expansion device within the cavity by aligning an orientation indicator relative to a horizontal or vertical plane.

12. The method of claim 11, wherein the orientation indicator comprises a transparent portion of the shell of the tissue expansion device, and the adjusting comprises aligning the orientation indicator relative to a vertical plane.

13. The method of claim 12, wherein the tissue expansion device comprises a plurality of tabs coupled to a posterior portion thereof, and wherein the orientation indicator is aligned with a first tab of the plurality of tabs located at a 6 o'clock position, and the adjusting comprises aligning the orientation indicator and the first tab relative to a vertical plane.

14. The device of claim 1, wherein the orientation indicator extends along a center position of the expandable shell.

15. The device of claim 1, wherein the expandable shell comprises a smooth exterior surface.

16. A method of manufacturing a tissue expansion device, the method comprising:
dipping a casting tool into a polymer solution to form a shell along an outer surface of the casting tool, the casting tool outer surface having a textured portion and a smooth portion;
permitting the shell to dry; and
removing the shell from the casting tool, the shell having an inner surface comprising a first portion corresponding to the textured portion and a second portion corresponding to the smooth portion, the shell having a smooth outer surface, wherein the smooth outer surface of the shell and the second portion collectively define a transparent orientation indicator, and wherein the smooth outer surface of the shell and the first portion of the shell inner surface collectively define a translucent or opaque textured vertical strip section of the shell that is adjacent to second portion and visually contrasts against the transparent orientation indicator, wherein the orientation indicator extends across at least 50% of a diameter of the expandable shell.

17. The method of claim 16, further comprising coupling a plurality of tabs to a posterior portion of the shell.

18. The method of claim 17, wherein a first tab of the plurality of tabs comprises an attribute different from an attribute of a remainder of the plurality of tabs, and wherein the method further comprises positioning the first tab at a 6 o'clock position on the posterior portion of the shell.

19. The method of claim 16, further comprising coupling an injection reservoir assembly to the shell inner surface at an injection port section of the shell inner surface to change the translucent or opaque section to transparent along the injection port section.

20. The method of claim 16, further comprising coupling a stable base to the shell inner surface along a posterior portion of the shell to change the translucent or opaque section to transparent along a section of the posterior portion.

21. The method of claim 16, further comprising coupling an injection reservoir assembly to the shell inner surface at an injection port section of the shell, wherein coupling the injection reservoir assembly comprises aligning an outer perimeter of the injection reservoir with an end portion of the orientation indicator.

22. A tissue expansion device comprising:
an expandable shell forming an expanding chamber and having an anterior portion and a layer of polymer material forming a smooth interior surface;
an orientation indicator formed as a surface texture within the expandable shell along the layer of polymer material and adjacent to the smooth interior surface to permit the orientation indicator to be visible along the anterior portion of the expandable shell; and
an injection port, coupled to the anterior portion of the shell, in fluid communication with the chamber and configured to permit injection of fluid into the chamber from a hypodermic needle.

23. A tissue expander comprising an expandable shell formed from a layer of biocompatible polymer material and an orientation indicator formed along an interior surface of the expandable shell and visible along an anterior portion of the expandable shell, wherein, the orientation indicator comprises a surface texture adjacent to a smooth interior surface of the expandable shell such that, when the expandable shell is seen in front view, the orientation indicator extends vertically along a center line.

24. A tissue expansion device comprising an expandable shell having an orientation indicator and an injection port, the orientation indicator formed as a textured vertical strip adjacent to a smooth interior surface along an interior surface of the expandable shell, and the injection port being coupled to an anterior portion of the shell and in fluid communication with a chamber of the shell.

* * * * *

UNITED STATES PATENT AND TRADEMARK OFFICE
CERTIFICATE OF CORRECTION

Page 1 of 1

PATENT NO. : 11,160,630 B2
APPLICATION NO. : 16/571036
DATED : November 2, 2021
INVENTOR(S) : David J. Schuessler et al.

It is certified that error appears in the above-identified patent and that said Letters Patent is hereby corrected as shown below:

In the Claims

Claim 22, Column 18, Line 14, "expanding" should read --expandable--.

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*